(12) United States Patent
Pensel

(10) Patent No.: US 7,510,724 B2
(45) Date of Patent: Mar. 31, 2009

(54) MEDICAL APPARATUS

(75) Inventor: Juergen Pensel, Altstatten (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 1162 days.

(21) Appl. No.: 10/374,365

(22) Filed: Feb. 25, 2003

(65) Prior Publication Data

US 2003/0157151 A1    Aug. 21, 2003

Related U.S. Application Data

(63) Continuation of application No. 09/529,144, filed as application No. PCT/EP99/05455 on Jul. 30, 1999, now abandoned.

(30) Foreign Application Priority Data

Aug. 7, 1998    (CH)    ..................... 1645/98

(51) Int. Cl.
*A61F 13/00*    (2006.01)
*A61F 2/00*    (2006.01)

(52) U.S. Cl. ..................... 424/422; 424/423

(58) Field of Classification Search ....................... None
See application file for complete search history.

(56) References Cited

U.S. PATENT DOCUMENTS

| 4,357,142 | A |   | 11/1982 | Schall, Jr. et al. |          |
|-----------|---|---|---------|---------------------|----------|
| 4,596,574 | A | * | 6/1986  | Urist               | 424/422  |
| 4,722,870 | A | * | 2/1988  | White               | 428/621  |
| 4,784,160 | A | * | 11/1988 | Szilagyi            | 607/116  |
| 4,960,425 | A | * | 10/1990 | Yan et al.          | 623/8    |
| 5,380,298 | A | * | 1/1995  | Zabetakis et al.    | 604/265  |
| 5,531,735 | A |   | 7/1996  | Thompson            |          |
| 5,649,951 | A | * | 7/1997  | Davidson            | 606/198  |
| 5,681,575 | A | * | 10/1997 | Burrell et al.      | 424/423  |

FOREIGN PATENT DOCUMENTS

| EP | 0405284 A2    |   | 1/1991 |
|----|---------------|---|--------|
| EP | 0472413 A2    |   | 2/1992 |
| JP | 03124877 A    | * | 5/1991 |
| WO | WO 92/11043 A1| * | 7/1992 |
| WO | WO 95/19583 A1|   | 7/1995 |
| WO | WO 97/29778 A2|   | 8/1997 |

* cited by examiner

*Primary Examiner*—S. Tran
(74) *Attorney, Agent, or Firm*—Hodgson Russ LLP

(57) ABSTRACT

The invention relates to a medical apparatus having a special coating on its surface, notably its surface facing the surroundings. The coating has germ and/or dirt-repellant and/or bactericidal properties. Special embodiments of the invention include dirt and/or germ-repellant and/or antiseptic materials or surface structures and anti-electro-static and/or electrically heated materials.

22 Claims, 1 Drawing Sheet

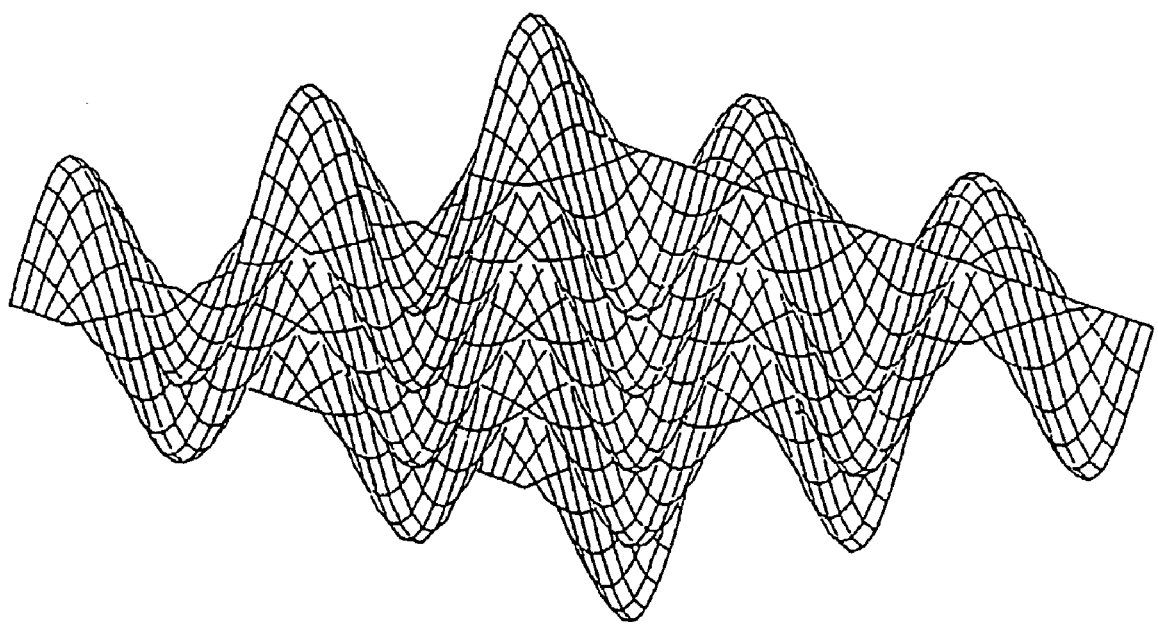

MEDICAL APPARATUS

CROSS-REFERENCES TO RELATED APPLICATIONS

The present application claims benefit of U.S. patent application Ser. No. 09/529,144 filed Apr. 7, 2000, which is the U.S. national phase under 35 U.S.C. 371 of International Application No. PCT/EP99/05455 filed Jul. 30, 1999 claiming priority of Swiss Patent Application No. 1645/98 filed Aug. 7, 1998.

BACKGROUND OF THE INVENTION

1. Field of the Invention

The invention relates to medical devices with a surface exposed in particular to the surrounding environment, and in particular a microscope, preferably a surgical microscope and/or its support. Explicitly not comprised in the invention are non-optical instruments for invasive interventions. Included, on the other hand, are optical devices and instruments like, for example endoscopes, laser scalpels, etc., scalpels or medical implants, plastic heart valves or similar items.

2. Description of the Related Art

It has always been a goal during operations and/or in the area of medical research to work in as sterile a manner as possible. That means the patient to be operated on and/or the subject involved in research is as much as possible not to be contaminated by germs (bacteria, viruses, fungi, etc.). Moreover, by completely preventing or removing any impurities, in particular protein substances, allergic reactions by the patient can be prevented, should he accidentally or unprotectedly come into contact with the medical devices. This is normally achieved by meticulously cleaning or sterilizing the surfaces of the medical devices. Those surfaces that do not sterilize well are covered with sterile cloths or sheets. With the operating microscope a "drape" typically must completely envelop or screen the surface of the microscope and support, at least in the sterile area around the patient. A drape of this kind is described, for example, in the German patent specification DE-A1-44 13 920. The drape is as a rule a disposable article so that using it is also connected with costs and with a direct environmental impact. The disposal of disposable articles from an operating room is expensive.

Aside from the fact that the covering and sterilization of the contaminated material, not to mention its disposal, is a time-consuming and costly process, there is always the danger of remaining unsterile gaps. Moreover, drapes as a rule reduce the optical qualities of microscopes, since they necessarily also enclose the lens along with the other parts. The cover glasses used for this can only be poorly steam-sterilized. Moreover, the covers restrict freedom of movement and visibility in the sterile area.

Olympus has brought microscope models CHK2 and CHL2 on the market, the optical parts of which are continually overflowed during manufacture with a thin vaporous antifungal gas that effectively prevents the growth of funguses for a period of three years. A tightly sealed binocular body is even more extensively protected against the onset of fungus because neither impurities nor moisture can intrude into the microscope. This antifungal arrangement involves a protection of the optical parts since fungus often leads to damage of the optical parts of a microscope, especially in tropical regions. In this respect the antifungal coating of the lens provided by Olympus is an improvement, but the sterility of the microscope is not improved. Only the service life of the lens or its optical characteristics are extended. The protection of patients was not within the purview of the producer for this type of antifungal outfitting.

BRIEF SUMMARY OF THE INVENTION

Pursuant to efforts to simplify and increase sterility, the object of the invention is to find measures for simplifying or improving the cleaning and/or the sterility of medical devices.

The object of the invention is fulfilled by applying the features of claim 1.

Coverings can be done away with and safety can be further increased even under sterile conditions by a special design and/or coating of the surface or material of the medical devices so that said surface or material has a germ-repellent or dirt-repellent effect.

Germ-repellent coatings are already known specifically in the area of medical implants, such as synthetic heart valves, prostheses, etc., but no one has yet publically contemplated using these measures known per se also on medical devices, in particular microscopes and their supports, where the above required or described effects according to the invention are produced.

Preferred additional embodiments of the invention or variants of these additional embodiments are described, or placed under patent protection, in the dependent claims.

BRIEF DESCRIPTION OF THE DRAWING

FIG. 1 is a magnified perspective view showing an example of a surface formed according to the present invention.

DETAILED DESCRIPTION OF THE INVENTION

By employing a germ/dirt-repellent and/or germicidal surface of the medical devices modified according to the invention, the danger of contamination and/or the danger of allergic reaction is reduced, should there be any contact between the surface of the device and the patient.

In addition the cleaning of the devices, especially the lens, is made substantially easier. Also advantageous here is an antiseptic surface or material composition as well as, additionally or alternatively, a surface that is generally dirt-repellent. Falling under the term "dirt" here are all contaminations of the surface by germ infestation and/or by aseptic materials and substances—such as water, fat, protein, etc.

One possibility for the production and selection of materials, in particular with optical glasses and or plastics, including the protective glass/plastic of microscopes is the doping according to the invention of said glasses/plastics with metals or metallic salts, in particular heavy metallic salts, such as silver or copper, zinc, nickel, manganese, cadmium, platinum salts or even, for example, salts of semi-metals, such as boron salts or similar items that—as known per se—act in particular as bactericides, fungicides and virocides. The effect involved here is often produced by metal ions, for example silver ions that can be given off against the germs.

Also the structure of the surface of materials such as housings, supports and in particular of optic glasses/plastics can be formed so as to offer as little support as possible to any kind of adhesive or cohesive forces on the part of septic or aseptic impurities and/or liquids. A fungistatic or fungicidal formation is therefore also advantageous for optical components in the interior of the microscope—as known per se—for example for use in the tropics. A dirt-repellent design is also advantageous here for protection of optical quality when it comes to optical components in the interior of the microscope. As a variant of this, the optical glass/plastic parts could also be coated—e.g. by vapor-deposition—with a very thin coating of a transparent plastic or ceramic material. Also materials from microsystem technology such as silicium, metal-ceramics, metals and plastics such as TEFLON® (polytetrafluoroethylene or PTFE)/silicone, etc. come into play here.

To increase the rigidity and toughness, there are high-density ceramics as microscope chassis known per se according to EP-B1-90967. A reference to the object of the invention presented in the preamble cannot be inferred from it.

The coating of parts with specific substances is known in principle, as for example:

color like coating to produce a pleasant appearance, such as hammer dimple enamel coating to increase surface strength;

coating with anti-oxidants and light stabilizers, e.g. as described in EP-A1-745 646;

coating of a lens support with synthetic polymers for bio-processes, e.g. as described in U.S. Pat. No. 4,357,142;

chroming of surfaces to increase surface strength, etc.

TEFLON® coated lenses, or lens housings are also known per se, but these known coated lenses were developed for other purposes, including lenses for inversion microscopes that can be immersed in Petri dishes and thus come into contact with liquid media. The TEFLON® coating applied in that case has essentially three purposes:

1. To inhibit mechanical abrasion (scratch-proofing) of the lens

2. To give the lens an increased resistance to corrosion

3. To prevent any metal ions of the lens housing from migrating into the liquid medium through a chemical-physical process (chemical protection of the medium from the lens being immersed).

Aside from the fact that the hydrophobic property of TEFLON® was naturally accepted as a welcome feature, this becomes obvious for the type of the liquid media. The technique by which the inversion microscope of this type came into use was named among other things the "patch-clamp technique."

However, a coating for the purposes indicated in the preamble for medical devices has never yet been suggested.

In the use of ceramics as per the invention, sintered ceramics and/or metal ceramics are contemplated, their surface being formed such that it is germ and/or dirt-repellent. One skilled in the art thus has to take into consideration certain geometric dimensions that have more favorable or unfavorable characteristics for corrosion by septic or aseptic impurities. Although every microstructure must have a certain structure, it will appear to the observer as a "smooth surface" to which nothing sticks. Metal ceramics, $Al_2O_3$ and AlN are best suited for a vapor deposition according to the invention.

One skilled in the art can thus select from a filling of ceramic materials that are known per se, this including in principle also modern materials such as glass metals with an alloy containing nickel, zircon and titanium. The atoms of such glass metals have not formed a regular crystal lattice. They are arranged randomly, resulting in an amorphous structure. C/SiC-bonded ceramics, as are used for example for mirror structures, can also come into use as oxide ceramics.

In a special surface formation according to the invention—primarily also for ceramic surfaces—the following principle is employed: The surface is physically (e.g. chemically and/or micro-mechanically) structured such that undesirable substances cannot adhere. A possible configuration thus provides the intentional arrangement of elevations with specific geometric dimensions that offer substances (e.g. liquids) no support on the surface due to their surface tension. The substances therefore cannot exert any adhesive forces on the surface.

Comparable effects are known in nature, e.g. in the natural surface formation of lotus leaves (surface structure) or on alchemilla conjuncta leaves (coated with very fine fuzz) on which water beads up without dampening the leaf when picking up any kind of adjacent dirt particles.

Aside from the prevention of adhesion, these surfaces are also especially easy to clean, since due to the adhesive forces of cleaning fluids—which themselves cannot react with the surface—dirt particles that might be lying on the surface are bonded to the drops of cleaning fluid and thereby rinsed away.

A surface with the following geometric structure is indicated as an example of such a surface structure (in some cases it does not have to be in a mathematically exact configuration):

$$Sin(x) \times Cos(y).$$

The resulting surface has a regular mound structure, the peaks of which preferably have the following interval: 1-100 µm, in particular 3-60 µm.

Alternatively, the elevations can also have a cubic or conical structure.

The invention nevertheless also encompasses mixed forms that one skilled in the art can determine in routine experiments.

The effectiveness of such surfaces formed according to the invention can be strengthened by combination with other measures according to the invention, such as a germicidal dressing (e.g. metal or metallic salt coating).

A particular embodiment is attained by making the micro-mechanical elevations out of various elements (especially metals or half metals), which in some cases are electrically isolated from one another, so that in addition to the mechanical and biocidal characteristics of the corresponding metals, there are also electrical or electrolytic effects that have an especially toxic or repellent action for particular germs.

Another possibility for treating standard devices, in particular supports, according to the invention is coating them with the matrix of a carrier material in which germicidal or germ-repellent substances are incorporated. Falling under germicidal substances here are all of those substances that have been traditionally used or will be used in the future to kill germs or to disinfect. These can be the aforesaid metallic salt compounds, but can also be alcohols, oxidizing materials, cell-membrane-damaging polyelectrolytes—e.g. tenside, etc.—or mixtures thereof.

This configuration according to the invention stands to a certain degree in contrary juxtaposition to the coatings according to the above-mentioned EP-A1-745 646.

"Supporting materials" are to be understood here as all of those materials that are suited to absorb other materials, namely germicidal substances. These can be foams or fabrics or other structures in which the said substances can be incorporated, integrated or attached. In the broadest sense, the matrix of the supporting material can also be constituted such that it supports on its surface germicidal substances, germ-repellent substances and the like. Consequently, such supporting materials can be constituted of plastic, rubber, lacquers, ceramics, etc. For example, this can also be an anti-fouling lacquer, which even today has germ-repellent and marine-plant-repellent properties, e.g. in boat construction.

Another idea, independent in and of itself, which can nevertheless be logically applied by itself or in combination with the previously mentioned ideas according to the invention, is to configure the surface or parts thereof—e.g. underlying parts—as electrically conductive. This is, on the one hand, so that the surface can thereby be configured as anti-static and, on the other hand, the surface can also, through the principle of resistance, be artificially brought to a germicidal temperature that kills at least heat-labile germs. In the electrostatic treatment of a surface according to the invention, there are several different factors to take into account, in particular the voltage ratios or electrostatic charging ratios in the surrounding environment. To attain electrical, electro-thermal or electrostatic characteristics, conductive material, e.g. carbon, can be integrated into the surface. Due to their antitoxicity, activated carbons with larger inner surface areas can possibly be used.

The anti-electrostatic coating of microscopes has been published in a patent by the applicant, e.g. in WO-A1-95/19583. Different microscopes, such as the LEICA MS5, MZ6 and MZ8 are on the market in the "ESD (electrostatic discharge) version." However, the object of the present invention is not resolved by this known anti-static coating, even if—by chance—the antistatic coating provided for the protection of electronic components also leads to a reduction of dust and dirt deposits on the devices. However, the contact sterility is still not fundamentally improved by this.

In another area, a retroreflector has already been treated by the applicant with a conductive coating for another purpose, namely heating up its surface to prevent the accumulation of ice and vapor condensation. See WO-A1-96/33428. A germicidal action was not yet provided for this.

In the use of the conductive resistance coating according to the invention, attention must be paid to the temperature stability of the supporting material. The purposive use of e.g. polymers with filler materials that increase thermal deformation resistance, for example mica, is suggested for this. A comprehensive article on various filler materials is indicated in "Kunststoffe [Plastics] 87 (1997) 9, Carl Hanser Verlag, Munich, pp. 1106-1112", which makes explicit reference to this.

The preferred application of various elements is placed under protection in claim 14.

The invention is not restricted to the individual inventive elements; on the contrary a combination of the same can produce symbiotic effects, i.e. antiseptic or germ/dirt-repellent effects.

For the purposes of this invention, "lens" is to be understood here as including all optical components such as glasses, plastics and also mirrors, which can be made of metal.

An example of a surface according to the invention is depicted in the drawing.

This shows as an example a sinusoidal/cosinusoidal-form surface with homogeneous elevations and indentations. A surface is formed as a function of the measures between the elevations so as to repel adhesive forces, or prevent the attachment and clogging of germs in a purely mechanical way. However, within the framework of the invention, one could also dispense with the downward-protruding valleys.

The elevations and valleys are drawn with grid lines for better visual representation.

Within the framework of the invention, there are also particular embodiments in which the elevations or valleys are constituted of different materials such that adjacent elevations are different, or such that parts of elevations differ. Thus, different materials are conceivable, especially various metals, along specific grid lines or along elevation lines (not shown), for example.

If the metals are isolated from each other, this results in electrolytic processes for ion-conductive substances coming into contact with said metals. The ion-conductive processes can furthermore have an anti-septic action.

What is claimed is:

1. A medical device comprising:
    a surgical microscope defining a surface exposed to the surrounding environment, said surface being passively germiphobal by having a plurality of elevations or indentations spaced from one another to achieve a lotus blossom effect.

2. The medical device according to claim 1, wherein said germiphobal surface is formed on said surgical microscope by a germ repellent coating.

3. The medical device according to claim 1, wherein said surgical microscope further includes optical glass or optical plastic doped with an antiseptic substance.

4. The medical device according to claim 3, wherein said optical glasses or optical plastics are doped with salts of a heavy or semi-heavy metal.

5. The medical device according to claim 3, wherein said surgical microscope further includes optical glass or optical plastic doped with boron.

6. The medical device according to claim 1, wherein said germiphobal surface is water-repellent.

7. The medical device according to claim 1, wherein said germiphobal surface is fat-repellent.

8. The medical device according to claim 1, wherein said germiphobal surface is protein-repellent.

9. The medical device according to claim 2, wherein said germ repellent coating is a ceramic coating.

10. The medical device according to claim 1, wherein said germiphobal surface is electrically conductive.

11. The medical device according to claim 10, wherein said exposed surface is anti-static and is grounded or connected to an adjustable electrical power source, whereby the electrostatic attraction of free particles from said surrounding environment is stopped or said free particles are repelled.

12. The medical device according to claim 10, wherein said germiphobal surface is electrically heatable by resistance heating to 60° Celsius.

13. The medical device according to claim 1, wherein said exposed surface is provided with a plurality of elevations or indentations, each of said plurality of elevations or indentations having a respective vertex, and the distance between vertices of adjacent elevations or indentations being in the range of 1-100 μm.

14. The medical device according to claim 13, wherein the distance between said vertices of adjacent elevations or indentations is in the range of 3-60 μm.

15. The medical device according to claim 13, wherein each of said plurality of elevations or indentations comprises a cubic structure with straight edges.

16. The medical device according to claim 13, wherein each of said plurality of elevations or indentations comprises a cylindrical structure.

17. The medical device according to claim 13, wherein each of said plurality of elevations or indentations comprises a frusto-conical structure.

18. The medical device according to claim 13, wherein said plurality of elevations or indentations are sinusoidal/cosinusoidal in form wherein height is determined according to the formula $\sin(x)\cos(y)$.

19. The medical device according to claim 18, wherein x and y are in the range of 1-100 μm.

20. The medical device according to claim 19, wherein x and y are in the range of 3-60 μm.

21. The medical device according to claim 2, wherein said germ repellent coating is a plastic coating.

22. The medical device according to claim 2, wherein said germ repellent coating is a lacquer coating.

* * * * *